United States Patent [19]

Ulbrich

[11] 4,101,648

[45] Jul. 18, 1978

[54] COMPOSITION FOR CARRYING OUT A URIC ACID LOAD TEST

[75] Inventor: Horst Ulbrich, Merenberg, Fed. Rep. of Germany

[73] Assignee: Dr. Eduard Fresenius Chemisch-pharmazeutische Industrie KG, Bad Homburg, Fed. Rep. of Germany

[21] Appl. No.: 716,549

[22] Filed: Aug. 23, 1976

[30] Foreign Application Priority Data

Aug. 22, 1975 [DE] Fed. Rep. of Germany ....... 2537488

[51] Int. Cl.$^2$ .................. A61K 29/00; A61K 31/52; G01N 33/16
[52] U.S. Cl. ...................................... 424/9; 424/180; 424/253
[58] Field of Search .................. 424/9, 180, 253; 23/230 R, 230 B

[56] References Cited

U.S. PATENT DOCUMENTS 3,737,524   6/1973   Ebel ................................. 424/180

OTHER PUBLICATIONS

Seegmiller, The J. of Clin. Invest., vol. 47, 1968, pp. 1193-1203.
Bendich, J. Biol. Chem., vol. 183, 1950, pp. 267-277.
Brown, et al., J. Biol. Chem., vol. 172, 1948, pp. 469-484.

*Primary Examiner*—Albert T. Meyers
*Assistant Examiner*—A. P. Fagelson
*Attorney, Agent, or Firm*—Fleit & Jacobson

[57] ABSTRACT

The invention relates to a composition for carrying out a uric acid load test for the differential diagnosis of diseases of the purine metabolism. The composition comprises a mixture of adenine and guanine, preferably in equal quantities, incorporated in a carrier, preferably comprising amorphous silicic acid.

2 Claims, No Drawings

COMPOSITION FOR CARRYING OUT A URIC ACID LOAD TEST

The invention relates to an agent for carrying out a uric acid load test.

The differential diagnosis of diseases of the purine metabolism, such as primary gout, secondary gout, hyperuricaemia and other arthritic diseases has hitherto been extraordinarily difficult and in many cases even impossible because the biorhythmic precept of the blood level of uric acid and the uric acid secretion in the urine in many cases fails to give an adequate pathognomonic parameter.

The serum value of uric acid in a patient depends on many factors, namely the actual current nourishment situation, the time of day, the uric acid-albumen bond in the serum, the daily cell decay rate, the uric acid secretion, the actual situation of the acid-base condition, the intake of certain medicines (e.g. carboanhydrase inhibitors, salicylates, probenecid, ACTH, cortisone derivatives, cinchophenes, carinamides and the like) and the rate of crystallizing out in the interstitial or intra-articular space.

For this reason, uric acid values measured on one occasion for a different uric acid-pool quantity could under certain circumstances be normal even under pathological conditions and conceal a disease, make a differential diagnosis more difficult or even impossible.

Uric acid load tests are already known.

In one method, loading takes place orally or with a probe with 1.0 g uric acid in 10 ml glycerine. Thereafter, the 24-hour urine is examined for uric acid secretion and compared with a 24-hour uric acid secretion without load serving as an unloaded value (Bartelheimer, Küchenmeister 'Clinical Functional Diagnostics', Thieme-Verlag, Stuttgart, 1973).

In another method of investigation, the measurement of the purine nucleotide conversion in the organism takes place after a parenteral dose of $C^{14}$ glycine. Urine is collected for seven days and the isolated uric acid tested for radio-activity. With essential gout and also with glycogenosis, the radio-activated uric acid rises to three times the normal after 2 to 3 days and in the presence of a Lesh-Nyhan syndrome to at least ten times the normal ('Matthes, Purine and Pyrimidine Metabolsim', Georg Thieme Verlag, Stuttgart, 1975).

With the supply of nucleic acids in doses of up to 4 g ribonucleic acid daily, Griebsch and collaborators discovered an increase in the serum uric acid concentration and the uric acid elimination depending on the dose.

The aforementioned methods are not, however, satisfactory. With the first-mentioned method, the synthesis of the uric acid is evaded and thus no true loading of the organism is achieved. Further, the nucleic acid metabolism is only marginally apprehended and therefore not the cause of hyperuricaemia which must be interpreted in the sense of the over-production theory. In addition, the collection of the 24-hour urine for two days is expensive. The second stated investigation with radioactively marked glycine is confined to special laboratories. In the last-mentioned method, where pure ribonucleic acid is supplied, it is assumed that the mechanism for the enzymatic separation of the ribonucleic acid is unimpaired, i.e. that all stomach or intestinal functions required for the dissociation of the ribonucleic acid are intact.

It is the object of the invention to provide an agent for carrying out an easily manipulatable uric acid load test which is not associated with the aforementioned disadvantages of known methods.

The invention is based on the discovery that this object can be achieved by an agent consisting principally of guanine and adenine.

The subject of the invention is an agent for carrying out a uric acid load test that is characterised in that it contains guanine and adenine and possibly conventional carrier and auxiliary substances.

Preferably, guanine and adenine are present in equal quantities.

The agents serve for the differential diagnosis of all unexplained conditions of pain and joint disturbances within the scope of rheumatoid illnesses, gout ailments being apprehended regardless of whether in an individual case one has to assume the renal gout theory or the over-production theory. Further, one apprehends the secondary hyperuricaemia and the gout kidney parallel to the severity of the kidney insufficiency.

Another advantage resides in the fact that pure starting substances are employed so that reproducible results can be obtained. Since the biological starting products guanine and adenine are being provided as a load rather than the uric acid itself, one also apprehends those groups of diseases in which the disturbances leading to hyperuricaemia or to gout can already be recognized in an increased biosynthesis of nucleic acid. It is of particular importance that one also apprehends those hyperuricaemia conditions that may be present either alone or in combination with a kidney section malfunction.

The uric acid load test can, for example, be carried out in the following manner.

Prior to loading, a determination of the uric acid is carried out as an unloaded value. On the evening prior to the second serum uric acid determination, the most favourable time being between 18.00 and 20.00, the agent is dispensed orally, for example with a little liquid. However, other methods of dispensing are also feasible. The dose amounts to about 2 g of purine bases. This corresponds to a dose of about 4 g of desoxyribonucleic acid. For example, seven capsules can be dispensed, each containing 140 mg guanine and 140 mg adenine.

12 to 15 hours after taking the capsules, the second uric acid determination takes place, the most favourable time of day being between 8.00 and 10.00.

If this second uric acid value lies within the normal range, as does the first value, primary or secondary gout or hyperuricaemia can be discounted. However, if the second uric acid value falls within pathological ranges above 7.0 to 8.0 mg/100 ml uric acid or even 30 to 50% and possibly still more above the unloaded value, then this indicates the presence of hyperuricaemia or gout requiring treatment.

24 to 36 hours after taking the capsules, a third uric acid determination is conducted, the most favourable time being between 8.00 and 10.00 on the next day. If the third value is still higher than the normal value, one must assume an additional disturbance of the renal uric acid elimination in the sense of a gout kidney.

It is preferred to dispense the agents orally in the galenical form of a hard gelatinous capsule because in this way one achieves rapid and complete resorption.

The agents preferably contain guanine and adenine in equal quantities. This is advantageous because each of the two substances activate a separate metabolic path in the metabolism of the purine body. Further, the combination of the two substances reduces the total toxicity of the test.

The agents may contain conventional carrier and auxiliary substances. Preferably, the agent contains amorphous silicic acid in an amount of about 1 to 20, preferably 5% by weight referred to the active substances.

I claim:

1. A composition for carrying out a uric acid load test comprising a mixture consisting essentially of adenine and guanine in about equal quantities by weight incorporated in amorphous silicic acid as a carrier therefor.

2. The composition of claim 1 which additionally also includes auxiliary substances.